(12) United States Patent
Chang et al.

(10) Patent No.: US 10,016,520 B1
(45) Date of Patent: Jul. 10, 2018

(54) COMPOUND AND PHARMACEUTICAL COMPOSITION FOR TUMOR IMAGING AND TUMOR THERAPY

(71) Applicant: SeeCure Taiwan Co., Ltd., Kaohsiung (TW)

(72) Inventors: Wei-Chung Chang, Kaohsiung (TW);
Kun-Hsin Lee, Kaohsiung (TW);
Kai-Chi Chang, Kaohsiung (TW);
Ping-Fan Chen, Kaohsiung (TW);
Min-Huei Huang, Kaohsiung (TW);
Hung-Yuan Huang, Kaohsiung (TW);
Ning Tsao, Kaohsiung (TW)

(73) Assignee: SeeCure Taiwan Co., Ltd., Kaohsiung (TW)

( * ) Notice: Subject to any disclaimer, the term of this patent is extended or adjusted under 35 U.S.C. 154(b) by 42 days.

(21) Appl. No.: 15/401,111

(22) Filed: Jan. 9, 2017

(51) Int. Cl.
| | | |
|---|---|---|
| A61K 31/196 | (2006.01) |
| A61K 31/198 | (2006.01) |
| A61K 51/04 | (2006.01) |
| A61K 31/519 | (2006.01) |
| A61K 31/337 | (2006.01) |
| A61K 31/4164 | (2006.01) |
| A61K 31/704 | (2006.01) |
| A61K 31/522 | (2006.01) |
| A61K 39/395 | (2006.01) |
| A61K 31/203 | (2006.01) |
| A61K 38/06 | (2006.01) |
| A61K 38/12 | (2006.01) |
| A61K 39/00 | (2006.01) |

(52) U.S. Cl.
CPC ........ *A61K 51/0497* (2013.01); *A61K 31/196* (2013.01); *A61K 31/198* (2013.01); *A61K 31/203* (2013.01); *A61K 31/337* (2013.01); *A61K 31/4164* (2013.01); *A61K 31/519* (2013.01); *A61K 31/522* (2013.01); *A61K 31/704* (2013.01); *A61K 38/06* (2013.01); *A61K 38/12* (2013.01); *A61K 39/3955* (2013.01); *A61K 2039/505* (2013.01)

(58) Field of Classification Search
None
See application file for complete search history.

(56) References Cited

U.S. PATENT DOCUMENTS 8,846,006 B2 * 9/2014 Frank ............... A61K 49/10
424/9.1
2009/0011986 A1 1/2009 Joshi et al.

FOREIGN PATENT DOCUMENTS

CN 102341127 2/2012
CN 103442737 12/2013

OTHER PUBLICATIONS

"Office Action of Taiwan Counterpart Application," dated Sep. 26, 2017, p. 1-p. 4.

* cited by examiner

*Primary Examiner* — Michael G Hartley
*Assistant Examiner* — Jagadishwar R Samala
(74) *Attorney, Agent, or Firm* — JCIPRNET

(57) ABSTRACT

A compound represented by formula (I) is provided, wherein in formula (I), $R_1$ and $R_2$ each independently represents hydrogen, O—$R_3$ or S—$R_4$, at least one of $R_1$ and $R_2$ is O—$R_3$ or S—$R_4$, and $R_3$ and $R_4$ are independently a $C_1$ to $C_{10}$ alkyl group, such that the $C_1$ to $C_{10}$ alkyl group is non-substituted or substituted with at least one selected from the group consisting of —OH, —$NH_2$, halogen, ester, ether, and carboxylic acid, and M being a metal or a metal-containing compound. The compound represented by formula (I) is shown to have higher specificity to tumor cells, and is therefore suitable for carrying anti-cancer drugs and/or nuclear imaging agents.

formula (I)

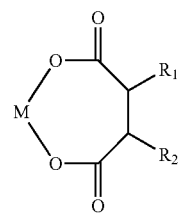

16 Claims, 9 Drawing Sheets

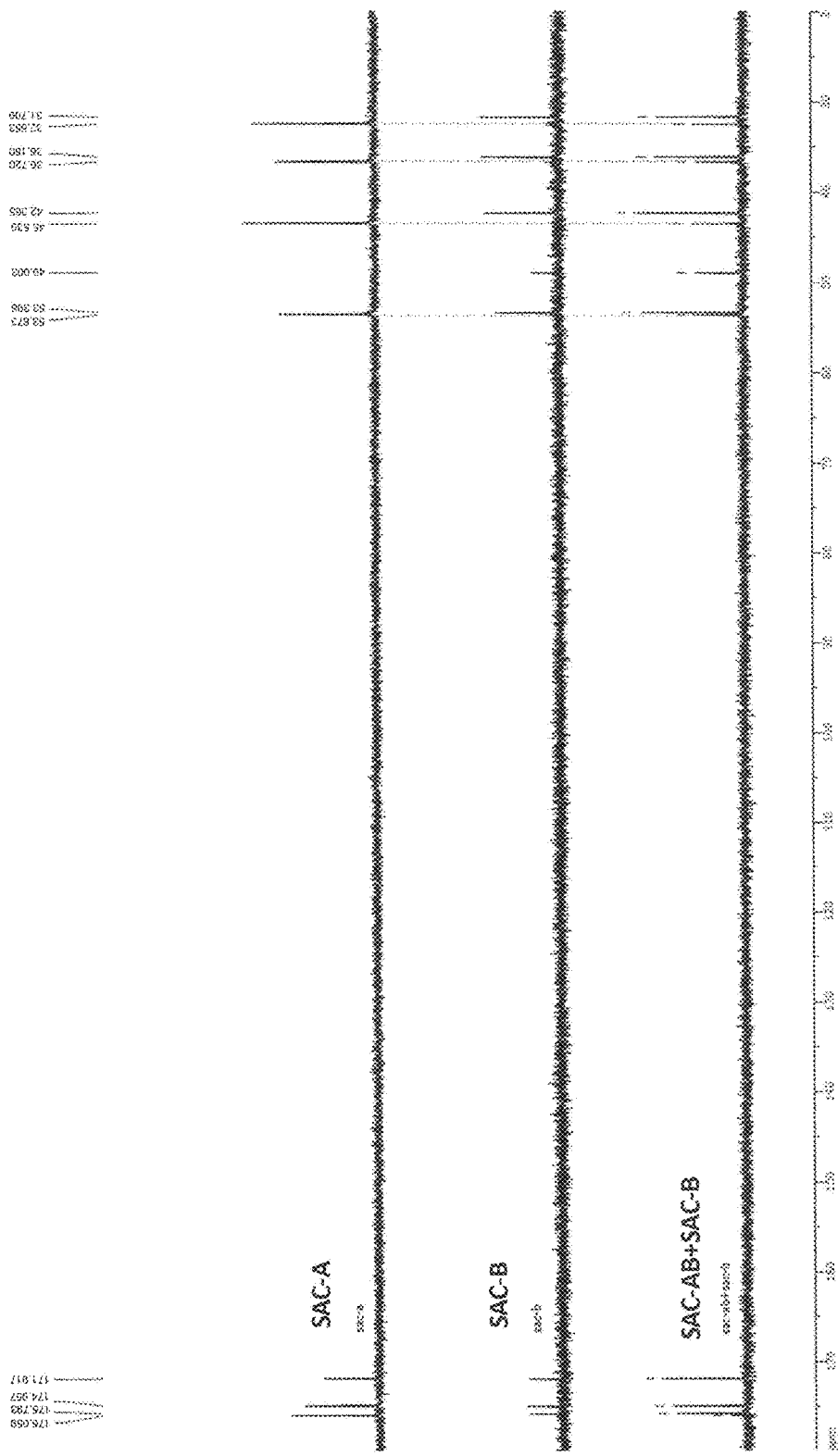

COMPOUND AND PHARMACEUTICAL COMPOSITION FOR TUMOR IMAGING AND TUMOR THERAPY

BACKGROUND OF THE INVENTION

1. Field of the Invention

The present invention generally relates to a compound and a pharmaceutical composition, in particular, to a compound and a pharmaceutical composition with improved specificity and efficiency for tumor imaging and tumor therapy.

2. Description of Related Art

There are a variety of cancer treatment methods available depending on the type and stage of cancer. In general, the treatments may involve the combination of chemotherapy, radiation therapy, hormone therapy, immunotherapy or surgery. The key to successful cancer treatment may require the identification of tumor through tumor imaging at an early stage, as well as targeted drug delivery during chemotherapy. Tumor imaging serves as the frontline in diagnosing cancer and allows us to trace and observe the efficacy of tumor therapy before and after the treatment. Nuclear imaging agents are conventionally used in tumor imaging for highlighting the existence and position of tumor. On the other hand, in order to eradicate cancer, anti-cancer drugs are commonly used to reduce the size of tumor and to prevent metastasis.

In tumor imaging and therapy, the specificity of the compound used in tumor imaging and tumor therapy is one of the most important factors that needs to be considered. For instance, compounds having high specificity for the tumor cells will provide good efficiency and accuracy in tumor imaging. Similarly, compounds having high specificity for the tumor cells will enable good efficacy of the anti-cancer drugs while reducing side effects during tumor treatment. In this regard, amino acid transporter system is found to be involved in improving the specificity of tumor imaging/therapy, as researchers have shown that the uptake of some amino acids are up-regulated in cancer cells. However, labeled amino acids are not widely applied in tumor imaging/therapy due to its high cost and complexity. Therefore, alternative compounds having improved specificity and efficiency for tumor imaging and therapy are desired.

SUMMARY OF THE INVENTION

Accordingly, the present invention provides a compound and a pharmaceutical composition that have improved specificity to tumor cells, and is suitable for carrying anti-cancer drugs and/or nuclear imaging agents.

The invention provides a compound represented by formula (I):

formula (I)

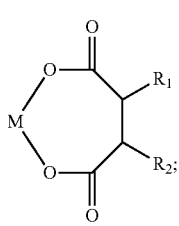

in formula (I), $R_1$ and $R_2$ each independently represents hydrogen, O—$R_3$ or S—$R_4$, wherein at least one of $R_1$ and $R_2$ is O—$R_3$ or S—$R_4$, and $R_3$ and $R_4$ are independently a $C_1$ to $C_{10}$ alkyl group, such that the $C_1$ to $C_{10}$ alkyl group is non-substituted or substituted with at least one selected from the group consisting of —OH, —$NH_2$, halogen, ester, ether, and carboxylic acid; and wherein M is a metal or a metal-containing compound.

In an embodiment of the invention, the metal or the metal-containing compound M is $^{99m}Tc$, $^{117m}Sn$, $^{188}Re$, $^{186}Re$, $^{90}Y$, $^{67}Ga$, $^{68}Ga$, $^{66}Ho$, $^{153}Sm$, $^{59}Fe$, $^{60}Cu$, $^{61}Cn$, $^{67}Cu$, $^{64}Cu$, $^{62}Cu$, $^{187}Re$, $^{89}Y$, $^{69}Ga$, $^{153}Pt$, $^{27}Al$, $^{56}Fe$, $^{64}Cu$, $^{118}Sn$, $^{10}B$, $^{58}Co$, $^{79}Se$, $^{40}Ca$, $^{64}Zn$, $^{57}Gd$, or a combination thereof.

In an embodiment of the invention, one of $R_1$ and $R_2$ is hydrogen and the other one is S—$R_3$.

In an embodiment of the invention, S—$R_3$ is cysteine.

In an embodiment of the invention, the compound is further represented by formula (II) or formula (III):

formula (II)

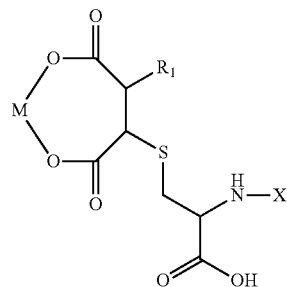

formula (III)

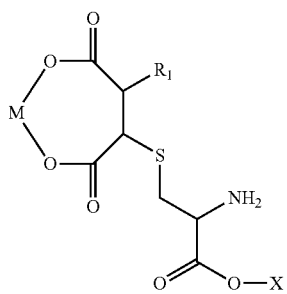

wherein in formula (II) and formula (III), X is an anticancer drug, an antiviral drug, an antibacterial drug, or a combination thereof.

In an embodiment of the invention, the drug X is melphalan, chlorambucil, methotrexate, paclitaxel, metronidazole, doxorubicin, penciclovir, ganciclovir, acyclovir, anti-EGFR antibody, anti-VEGF antibody, anti-PDGF antibody, retinoic acid, RGD peptide, or octreotide.

In an embodiment of the invention, the compound of formula (I) is obtained by conjugating the metal or the metal-containing compound M to a compound represented by formula (IV), formula (IV)

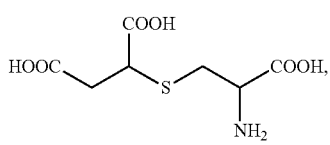

wherein the compound represented by formula (IV) has two stereoisomeric forms and only one of the stereoisomeric form is used for conjugation to the metal or the metal-containing compound M.

In an embodiment of the invention, the two stereoisomeric forms of formula (IV) is represented by formula (IV-a) and formula (IV-b):

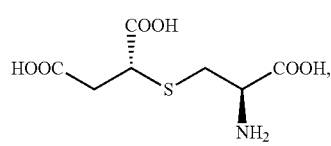

formula (IV-a)

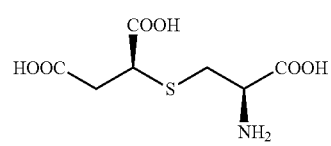

formula (IV-b)

wherein only the stereoisomeric form represented by formula (IV-a) is used for conjugation to the metal or the metal-containing compound M.

The invention further provides a pharmaceutical composition for tumor imaging and/or tumor treatment. The pharmaceutical composition includes a pharmaceutically-acceptable carrier, and a compound represented by formula (I):

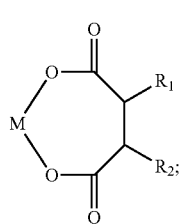

formula (I)

in formula (I), $R_1$ and $R_2$ each independently represents hydrogen, O—$R_3$ or S—$R_4$, wherein at least one of $R_1$ and $R_2$ is O—$R_3$ or S—$R_4$, and $R_3$ and $R_4$ are independently a $C_1$ to $C_{10}$ alkyl group, such that the $C_1$ to $C_{10}$ alkyl group is non-substituted or substituted with at least one selected from the group consisting of —OH, —$NH_2$, halogen, ester, ether, and carboxylic acid; and M is a metal or a metal-containing compound.

In an embodiment of the invention, the metal or the metal-containing compound M is $^{99m}$Tc, $^{117m}$Sn, $^{188}$Re, $^{186}$Re, $^{90}$Y, $^{67}$Ga, $^{68}$Ga, $^{166}$Ho, $^{153}$Sm, $^{59}$Fe, $^{60}$Cu, $^{61}$Cu, $^{67}$Cu, $^{64}$Cu, $^{62}$Cu, $^{187}$Re, $^{89}$Y, $^{69}$Ga, $^{153}$Pt, $^{27}$Al, $^{56}$Fe, $^{64}$Cu, $^{118}$Sn, $^{10}$B, $^{58}$Co, $^{79}$Se, $^{40}$Ca, $^{64}$Zn, $^{157}$Gd, or a combination thereof.

In an embodiment of the invention, one of $R_1$ and $R_2$ is hydrogen and the other one is S—$R_3$.

In an embodiment of the invention, S—$R_3$ is cysteine.

In an embodiment of the invention, the compound is further represented by formula (II) or formula (III):

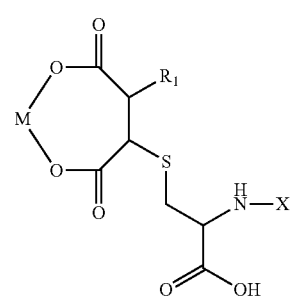

formula (II)

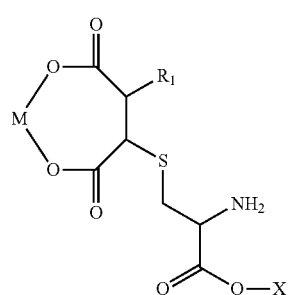

formula (III)

wherein in formula (II) and formula (III), X is an anti-cancer drug, an antiviral drug, an antibacterial drug, or a combination thereof.

In an embodiment of the invention, the drug X is melphalan, chlorambucil, methotrexate, paclitaxel, metronidazole, doxorubicin, penciclovir, ganciclovir, acyclovir, anti-EGFR antibody, anti-VEGF antibody, anti-PDGF antibody, retinoic acid, RGD peptide, or octreotide.

In an embodiment of the invention, the compound of formula (I) is obtained by conjugating the metal or the metal-containing compound M to a compound represented by formula (IV),

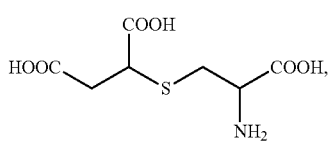

formula (IV)

wherein the compound represented by formula (IV) has two stereoisomeric forms and only one of the stereoisomeric form is used for conjugation to the metal or the metal-containing compound M.

In an embodiment of the invention, the two stereoisomeric forms of formula (IV) is represented by formula (IV-a) and formula (IV-b):

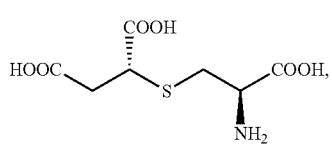

formula (IV-a)

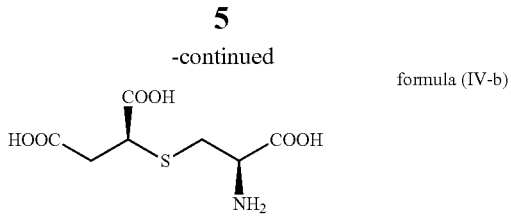

formula (IV-b)

wherein only the stereoisomeric form represented by formula (IV-a) is used for conjugation to the metal or the metal-containing compound M.

Based on the above, the compound and the pharmaceutical composition of the present invention have improved specificity to tumor cells, and is therefore suitable for carrying anti-cancer drugs and/or nuclear imaging agents.

In order to make the aforementioned features and advantages of the disclosure more comprehensible, embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

FIG. 4 shows the comparison of the $^{13}$C NMR spectrum of two stereoisomeric forms SAC-A and SAC-B of succinic acid-cysteine (SAC) prepared in Example 3 of the present invention.

DESCRIPTION OF THE EMBODIMENTS

Figure 1A:
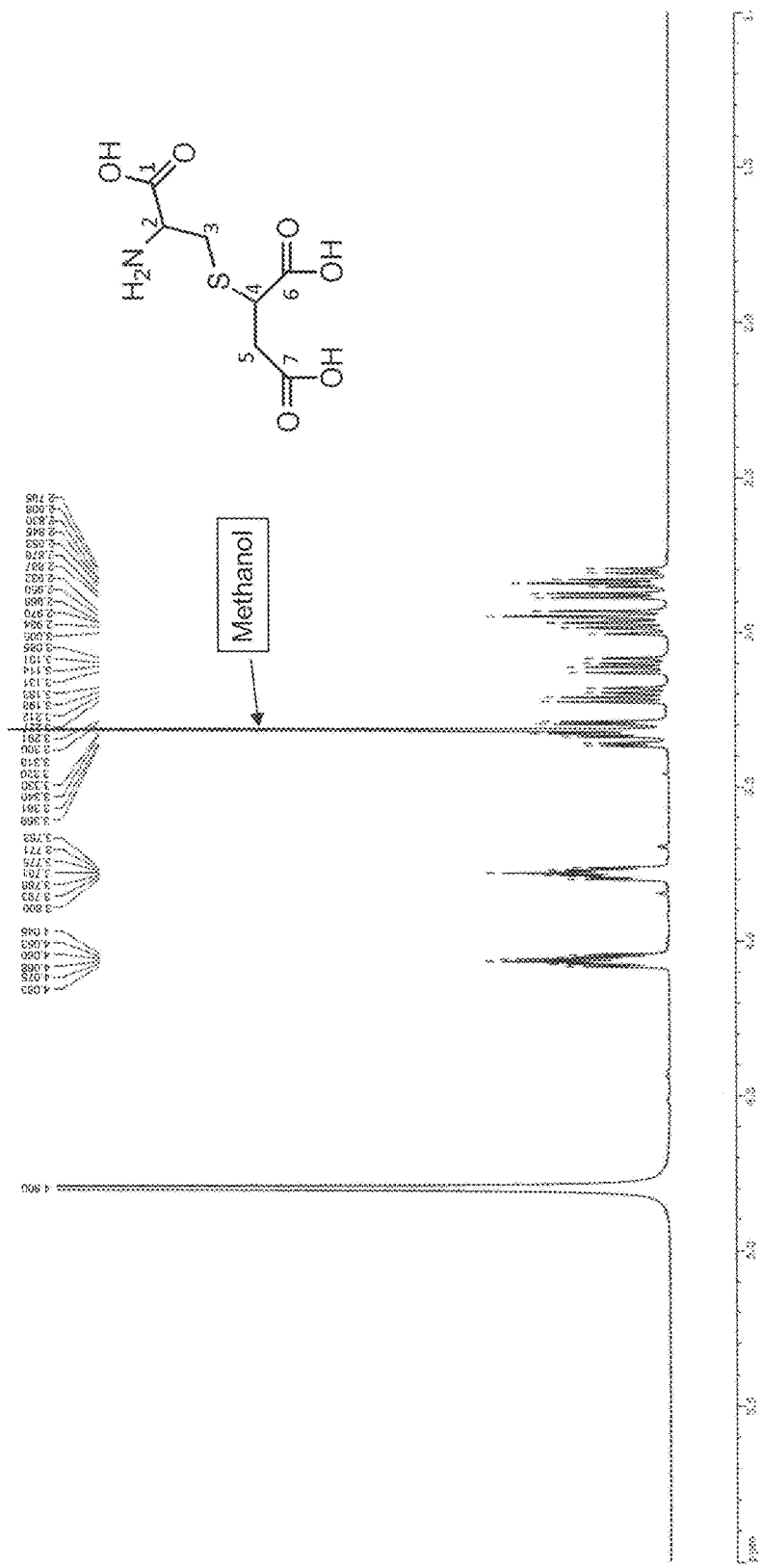
FIG. 1A shows the $^1$H NMR spectrum of the diastereoisomeric succinic acid-cysteine (SAC) prepared in Example 1 of the present invention.

Reference will now be made in detail to the present preferred embodiments of the invention, examples of which are illustrated in the accompanying drawings. Wherever possible, the same reference numbers are used in the drawings and the description to refer to the same or like parts.

The present invention provides a compound with good specificity to tumor cells, and is therefore suitable for carrying anti-cancer drugs and/or nuclear imaging agents. In an embodiment of the invention, the compound may be considered as a metallic-succinate based conjugate. In another embodiment of the invention, the compound may be considered as a succinate-cysteine based conjugate. Nevertheless, it is important to recognize that the term "metallic-succinate based conjugate" or "succinate-cysteine based conjugate" is merely used to describe the structure of compounds in specific embodiments of the invention, but do not serve to limit the compound of the present invention to these specific structures.

In the present embodiment, a compound of the present invention is represented by formula (I):

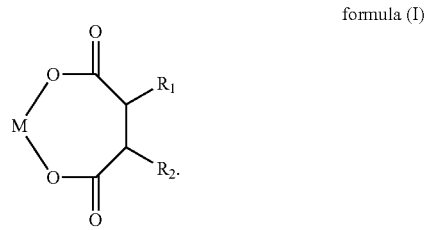

formula (I)

The compound represented by formula (I) is for example, a metallic-succinate based conjugate. In formula (I), $R_1$ and $R_2$ each independently represents hydrogen, O—$R_3$ or S—$R_4$, wherein at least one of $R_1$ and $R_2$ is O—$R_3$ or S—$R_4$, and $R_3$ and $R_4$ are independently a $C_1$ to $C_{10}$ alkyl group, such that the $C_1$ to $C_{10}$ alkyl group is non-substituted or substituted with at least one selected from the group consisting of —OH, —NH$_2$, halogen, ester, ether, and carboxylic acid. Furthermore, M is a metal or a metal-containing compound.

More specifically, the metal or the metal-containing compounds M are for example radiolabeled compounds that may be used as nuclear imaging agents. For instance, in an embodiment of the invention, the metal or the metal-containing compound M is $^{99m}$Tc, $^{117m}$Sn, $^{188}$Re, $^{186}$Re, $^{90}$Y, $^{67}$Ga, $^{68}$Ga, $^{166}$Ho, $^{153}$Sm, $^{59}$Fe, $^{60}$Cu, $^{61}$Cu, $^{67}$Cu, $^{64}$Cu, $^{62}$Cu, $^{187}$Re, $^{89}$Y, $^{69}$Ga, $^{153}$Pt, $^{27}$Al, $^{56}$Fe, $^{64}$Cu, $^{118}$Sn, $^{10}$B, $^{58}$Co, $^{79}$Se, $^{40}$Ca, $^{64}$Zn, $^{157}$Gd, or a combination thereof. However, the metal or the metal-containing compound M of the present invention is not particularly limited thereto, and can be any other metal or metal-containing compounds that are suitable for tumor imaging.

Furthermore, for the compound represented by formula (I), it is preferable that one of $R_1$ and $R_2$ is hydrogen and the other one is S—$R_3$, wherein S—$R_3$ is cysteine. Specific examples of such compounds of formula (I) may be further represented by formula (II) or formula (III) shown below.

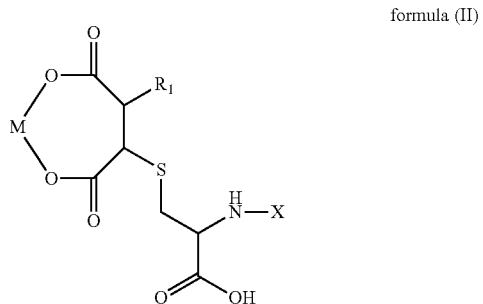

formula (II)

formula (III)

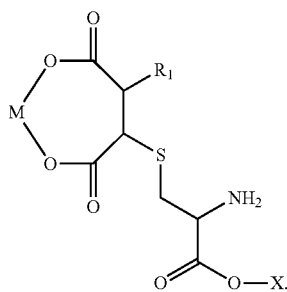

In formula (II) and formula (III), X is an anticancer drug, an antiviral drug, an antibacterial drug, or a combination thereof, whereas the metal or the metal-containing compounds M are similar to that of formula (I) described above. The compounds of formula (II) and formula (III) are suitable for use in tumor therapy, wherein the compounds have a succinate-cysteine based structure that is conjugated with different types of drug X depending on the purpose of treatment. For example, the drug X that may be conjugated to the succinate-cysteine based structure are such as melphalan, chlorambucil, methotrexate, paclitaxel, metronidazole, doxorubicin, penciclovir, ganciclovir, acyclovir, anti-EGFR antibody, anti-VEGF antibody, anti-PDGF antibody, retinoic acid, RGD peptide, or octreotide. Other suitable drugs may also be conjugated to the succinate-cysteine based structure based on requirement.

In an embodiment of the invention, the compound of formula (I) is obtained by conjugating the metal or the metal-containing compound M to a compound represented by formula (IV).

formula (IV)

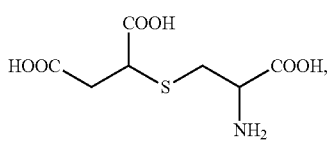

The compound of formula (IV), is a succinic acid-cysteine (SAC) with a chemical name of 2-amino-3-[(1,2-dicarboxyethyl)sulfanyl] propionic acid. More specifically, the compound of formula (IV) (or the SAC compound) has two stereoisomeric forms, and in the present embodiment, only one of the stereoisomeric form is used for conjugation to the metal or the metal-containing compound M.

In the present embodiment, the two stereoisomeric forms of formula (IV) is represented by formula (IV-a) and formula (IV-b):

formula (IV-a)

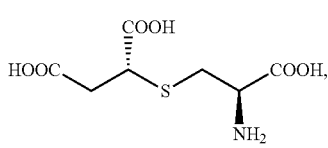

formula (IV-b)

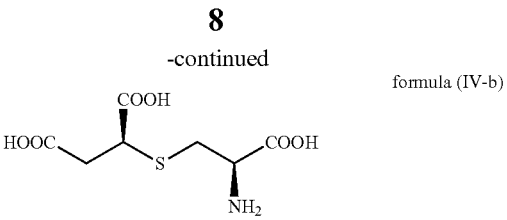

Furthermore, only the stereoisomeric form represented by formula (IV-a) is used for conjugation to the metal or the metal-containing compound M. In the present invention the compound represented by formula (IV-a) (herein abbreviated as SAC-A) was found to have higher radiolabeling purity than the other stereoisomeric form of formula (IV-b) (herein abbreviated as SAC-B). Therefore, the compound of SAC-A is more preferable than the other stereoisomers for use in tumor imaging and tumor therapy.

In the present embodiment, in order to obtain the compound represented by formula (I), the metal or the metal containing compound M is conjugated to the two carboxylic acid groups in the succinic acid-cysteine (SAC) compound of formula (IV). Although the compound of SAC-A is more preferable than the other stereoisomers for use in tumor imaging and tumor therapy, however, the other stereoisomers such as SAC-B or the mixture of the stereoisomers may still be used in tumor imaging and tumor therapy to achieve similar effects.

Furthermore, the succinic acid-cysteine (SAC) compound of formula (IV) is also suitable to be conjugated to the metal or the metal containing compound M and the drug X at the same time in order to obtain the compounds represented by formula (II) and formula (III) shown above. For example, the drug X may be reacted and attached through the amine portion of the cysteine in the SAC compound, or alternatively, be reacted and attached through the acid portion of the cysteine in the SAC compound. After attachment of the drug X to the SAC compound, the compound may be used in tumor therapy. For example, in tumors observed in neuroendocrine cancer, brain cancer, breast cancer, prostate cancer, colon cancer, lung cancer, liver cancer, pancreas cancer, gastric cancer, lymphoma and uterine tumor, cervical tumor, extremitis tumor, sarcoma, melanoma and many more.

Therefore, the SAC compound of the present invention may be suitable for conjugating to the metal or the metal containing compound M for use in tumor imaging, and suitable for conjugating to the drug X for tumor therapy (chemotherapy etc.) to obtain the compounds of the present invention. It is worth mentioning that the SAC compound (represented by formula (IV)) was set forth as a specific example of forming the compound represented by formula (I) of the present invention. However, the present invention is not limited thereto, and those compounds structurally similar to the compound of formula (I) may be used.

In addition, in another embodiment of the invention, the compound represented by formula (I) may be used in a pharmaceutical composition for tumor imaging and/or tumor treatment. For example, the pharmaceutical composition may comprise a pharmaceutically-acceptable carrier in combination with the compound represented by formula (I) described above. The pharmaceutically-acceptable carrier used may include but are not limited to water, phosphate buffered saline, alcohol, glycerol, chitosan, alginate, chondroitin, vitamin E, mineral oil, dimethyl sulfoxide (DMSO), cyclodextrin, polylactic acid, or a combination of the above.

The pharmaceutically-acceptable carrier may be appropriately selected based on the requirements of tumor imaging and/or tumor treatment.

To prove that the compounds of the present invention are suitable for carrying anti-cancer drugs and/or nuclear imaging agents, the compounds of the present invention are synthesized and tested by using the method described in the following examples.

Example 1

Synthesis of Succinic Acid-Cysteine (SAC)

The succinic acid-cysteine (SAC) or the compound represented by formula (IV) is synthesized using the method described in scheme 1 below.

Scheme 1: Synthesis of Succinic acid-cysteine (SAC)

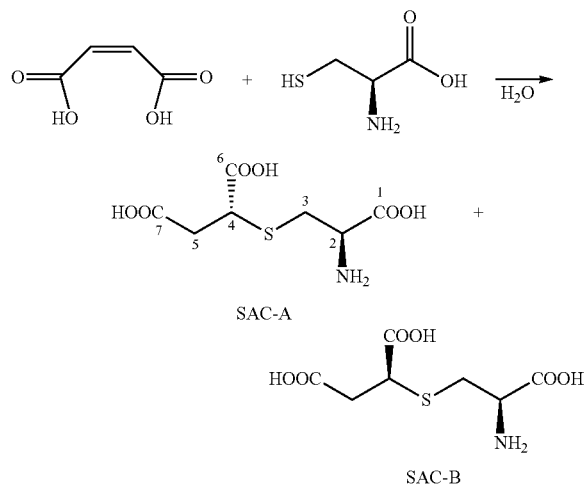

SAC-A

SAC-B

As shown in scheme 1, the SAC compound of example 1 is synthesized by the following process. Maleic acid (23.2 g, 0.2 mol) was added to a solution of L-cysteine (24.2 g, 0.2 mol) in water (1 L). The reaction mixture was stirred at room temperature for 24 hours, and acetone (3 L) was added thereto. The precipitate was collected by filtration and recrystallized from methanol to give a diastereoisomeric mixture (SAC-A+SAC-B; 32.9 g, 70% yield). The structure of the diastereoisomeric SAC compound was confirmed by $^1$H-NMR and $^{13}$C-NMR as shown in FIG. 1A and FIG. 1B.

Figure 1B:
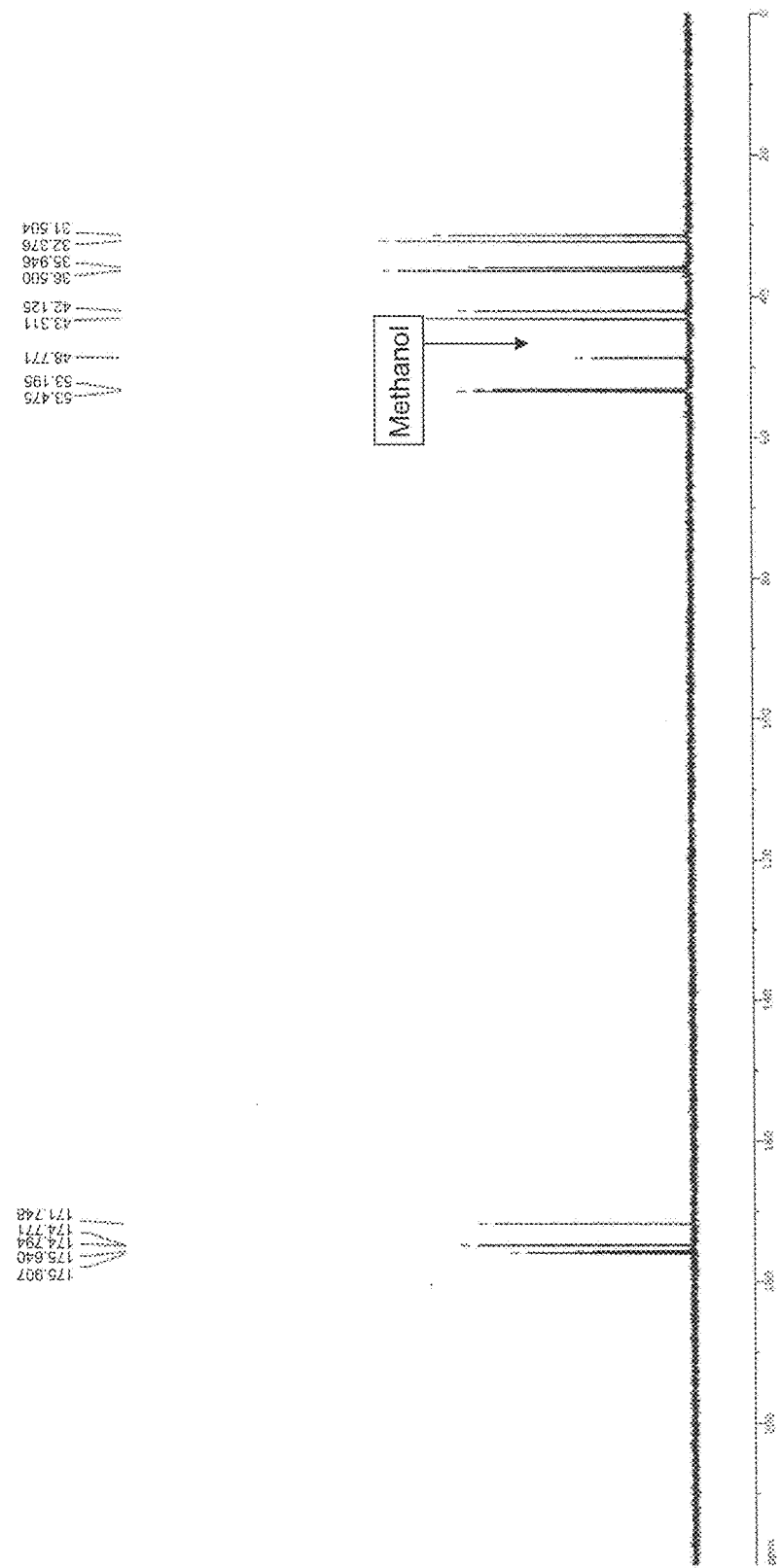
FIG. 1B shows the $^{13}$C NMR spectrum of the diastereoisomeric succinic acid-cysteine (SAC) prepared in Example 1 of the present invention.

Specifically, FIG. 1A shows the $^1$H NMR spectrum of the diastereoisomeric succinic acid-cysteine (SAC) prepared in Example 1 of the present invention. FIG. 1B shows the $^{13}$C NMR spectrum of the diastereoisomeric succinic acid-cysteine (SAC) prepared in Example 1 of the present invention. As shown in FIG. 1A, the proton shifts between 2.8 ppm to 3.3 ppm represents the protons attached to the carbon at the $3^{rd}$ position and $5^{th}$ position, while the proton shifts between 3.7 ppm to 4.1 ppm represents the protons attached to the carbon at the $2^{nd}$ position and the $4^{th}$ position. Furthermore, referring to FIG. 1B, the carbon at the $2^{nd}$, $3^{rd}$, $4^{th}$ and $5^{th}$ position have carbon shifts in between 32 ppm to 54 ppm, whereas the three carbonyl carbons at the $1^{st}$, $6^{th}$ and $7^{th}$ position have carbon shifts above 170 ppm. Based on the NMR results, the successful synthesis of the diastereoisomeric SAC compound (mixture of SAC-A and SAC-B) is confirmed.

The SAC compounds synthesized in the above example may be used for carrying anti-cancer drugs and/or nuclear imaging agents. As a specific example, the synthesis of the metallic-succinate based conjugates of $^{99m}$Tc-SAC, and $^{68}$Ga-SAC are described below.

Synthesis of $^{99m}$Tc-SAC and $^{68}$Ga-SAC

For $^{99m}$Tc-labeling, the diastereoisomeric SAC compound (5 mg) was dissolved in 0.2 mL of water, and Tin (II) chloride (0.1 mg) dissolved in 0.1 mL water and sodium pertechnetate Na$^{99m}$TcO$_4$ (1 mCi) was directly added to the SAC compound solution. Thereafter, the $^{99m}$Tc-SAC compound is obtained.

For $^{68}$Ga-labelling, the diastereoisomeric SAC compound (5 mg) was dissolved in 0.2 mL of water, and $^{68}$GaCl3 (5 mCi) was directly added to the SAC compound solution, followed by heating at 70° C. for 10 minutes. Thereafter, the $^{68}$Ga-SAC compound is obtained.

Radio-thin layer chromatography using three systems (acetone, saline, 1M NH$_4$Cl/MeOH (4:1) was used to analyze the radiochemical purity of $^{99m}$Tc-SAC and $^{68}$Ga-SAC. Radiochemical purity of $^{99m}$Tc-SAC and $^{68}$Ga-SAC analyzed by these systems were greater than 96%. The results above prove that the SAC compound is suitable for carrying nuclear imaging agents, and the $^{99m}$Tc-SAC and $^{68}$Ga-SAC compounds may correspond to the compound represented by formula (I) as described in the embodiments of the present invention.

Example 2

In-Vitro Cellular Uptake Studies

To verify that the compounds of the present invention are suitable for carrying anti-cancer drugs to targeted sites, the following in-vitro cellular uptake studies were performed.

Breast cancer cells (13762) from RBA CRL-1747 rat breast cancer cell line (American Type Culture Collection, Rockville, Md.) were used. The cancer cells were plated onto 12-well tissue culture plates at a concentration of 50,000 cells per well for carrying out the uptake studies. The cells were cultured in Eagle's MEM with Earle's BSS (90%) and fetal bovine serum (10%) under standard culture conditions (37° C., 95% humidified air and 5% CO$_2$). After seeding, the cells were incubated at 37° C. for 48 hours to allow for cell attachment and growth. After reaching approximately 70% confluency of cells, the cells are ready for use in the cellular uptake experiments.

Specifically, upon reaching 70% cell confluency, the growth media were aspirated and the cells were washed twice with phosphate buffered saline (PBS). Serum-free media and $^{99m}$Tc-SAC obtained in Example 1 were added to the cells for performing the cellular uptake experiment. Similarly, $^{99m}$Tc-succinate was used as a control and were added to the cells with the serum-free media. The cells with the added test compounds were incubated for 60 minutes with 5% CO$_2$ and 95% air at 37° C. To ascertain the subcellular distribution of $^{99m}$Tc-SAC, cell fraction assays (cytosol and nucleus) were performed at 60 min post-incubation. The cells were harvested by washing twice with phosphate-buffered saline (PBS) (0.5 ml) and detached using trypsin-EDTA (0.2 ml) for 5 minutes. After 5 minutes of incubation, PBS (0.5 ml) was added, and the total volume was transferred to a test tube for evaluation.

The radioactivity of the test compounds was counted using a Packard Cobra gamma counter (Downers Grover, Ill.). Data points represented an average of three measurements that were calculated as a percent uptake per number of viable cells. The results of the cellular uptake studies are presented in FIG. 2.

Figure 2:
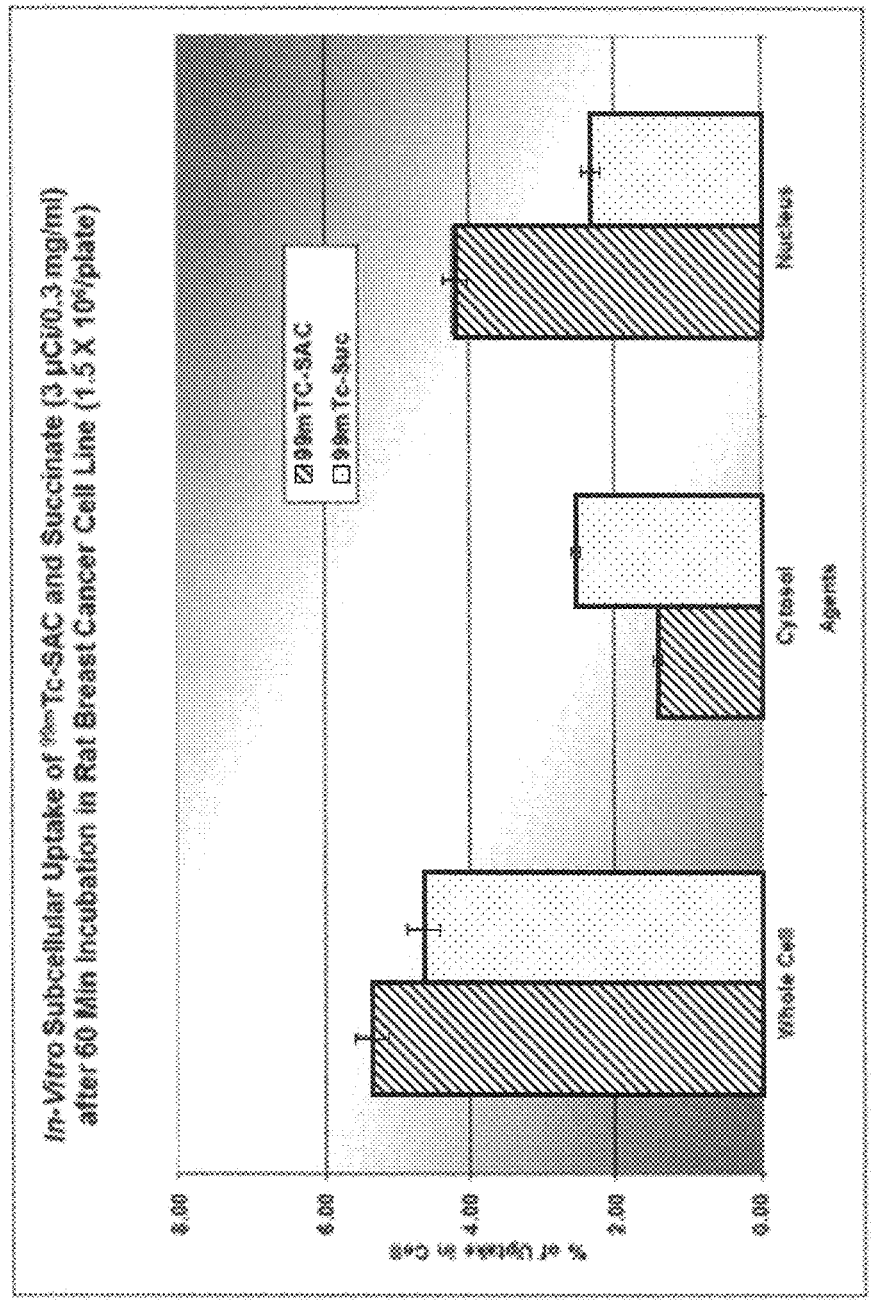
FIG. 2 shows the in-vitro subcellular uptake of $^{99m}$Tc-SAC and Succinate according to Example 2 of the present invention.

FIG. 2 shows the in-vitro subcellular uptake of $^{99m}$Tc-SAC and $^{99m}$Tc-succinate according to Example 2 of the present invention. From the results shown in FIG. 2, it can be seen that the cellular uptake of $^{99m}$Tc-SAC in the nucleus is approximately two times higher than the cellular uptake of $^{99m}$Tc-succinate in the nucleus. More specifically, approximately 75% of the $^{99m}$Tc-SAC cell uptake in the whole cell is located in the nucleus while only around 25% of the $^{99m}$Tc-SAC cell uptake in the whole cell is located in the cytosol. In comparison, approximately 50% of the $^{99m}$Tc-succinate cell uptake in the whole cell is located in the nucleus while the other 50% of the $^{99m}$Tc-succinate cell uptake is located in the cytosol. Clearly, these results prove that the $^{99m}$Tc-SAC compound is more successful for the cellular uptake into the cancer cell nucleus. As such, the $^{99m}$Tc-SAC is more promising for carrying anti-cancer drugs or other drugs to targeted sites with higher specificity and be used for tumor therapy.

Example 3

As noted above, the SAC compound (represented by formula (IV) may contain the stereoisomers SAC-A (formula (IV-a)) and SAC-B (formula (IV-b)). In the following example, the stereoisomers SAC-A and SAC-B were separated and purified, and their radiolabeling purity was compared.

Separation of the Succinic Acid-Cysteine (SAC) Compound Stereoisomers

The diastereoisomeric SAC compound prepared in Example 1 was used for separation. Specifically, 70 mg of the diastereoisomeric SAC compound was subjected to chromatography on Dowex 50W resin [200-400 mesh, 1.5× 90 cm, buffered with a pH 2.50 ammonia-formate buffer and eluted with a pH 2.70 buffer (5 mL fractions)]. Fractions which showed peaks at $t_R$ 18.5 and 19.5 minutes on HPLC were respectively combined and desalted using Dowex 50W to give the stereoisomers SAC-A (10 mg) and SAC-B (5 mg) respectively.

Figure 3A:
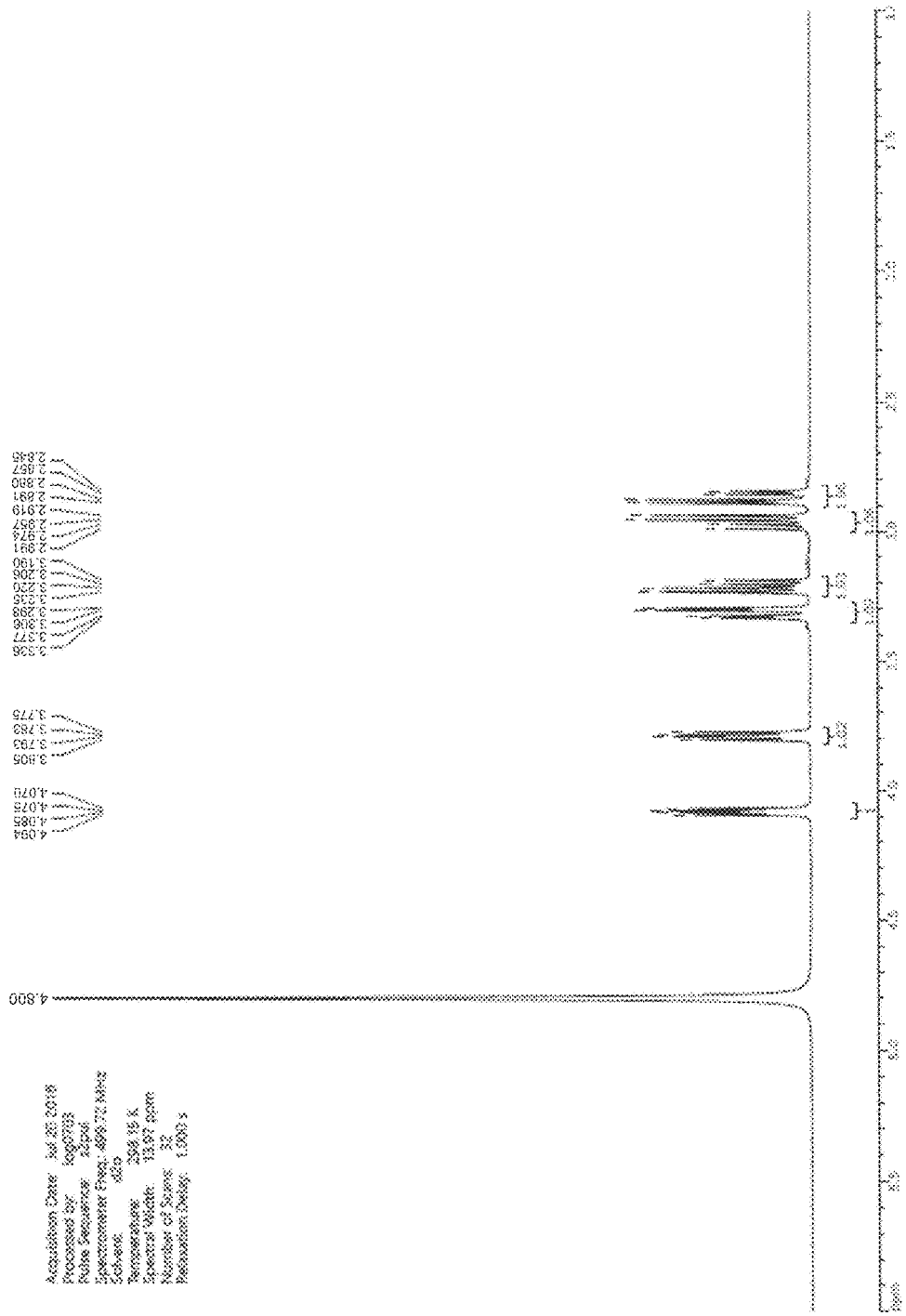
FIG. 3A shows the $^1$H NMR spectrum of the stereoisomeric form SAC-A of succinic acid-cysteine (SAC) prepared in Example 3 of the present invention.
Figure 3B:
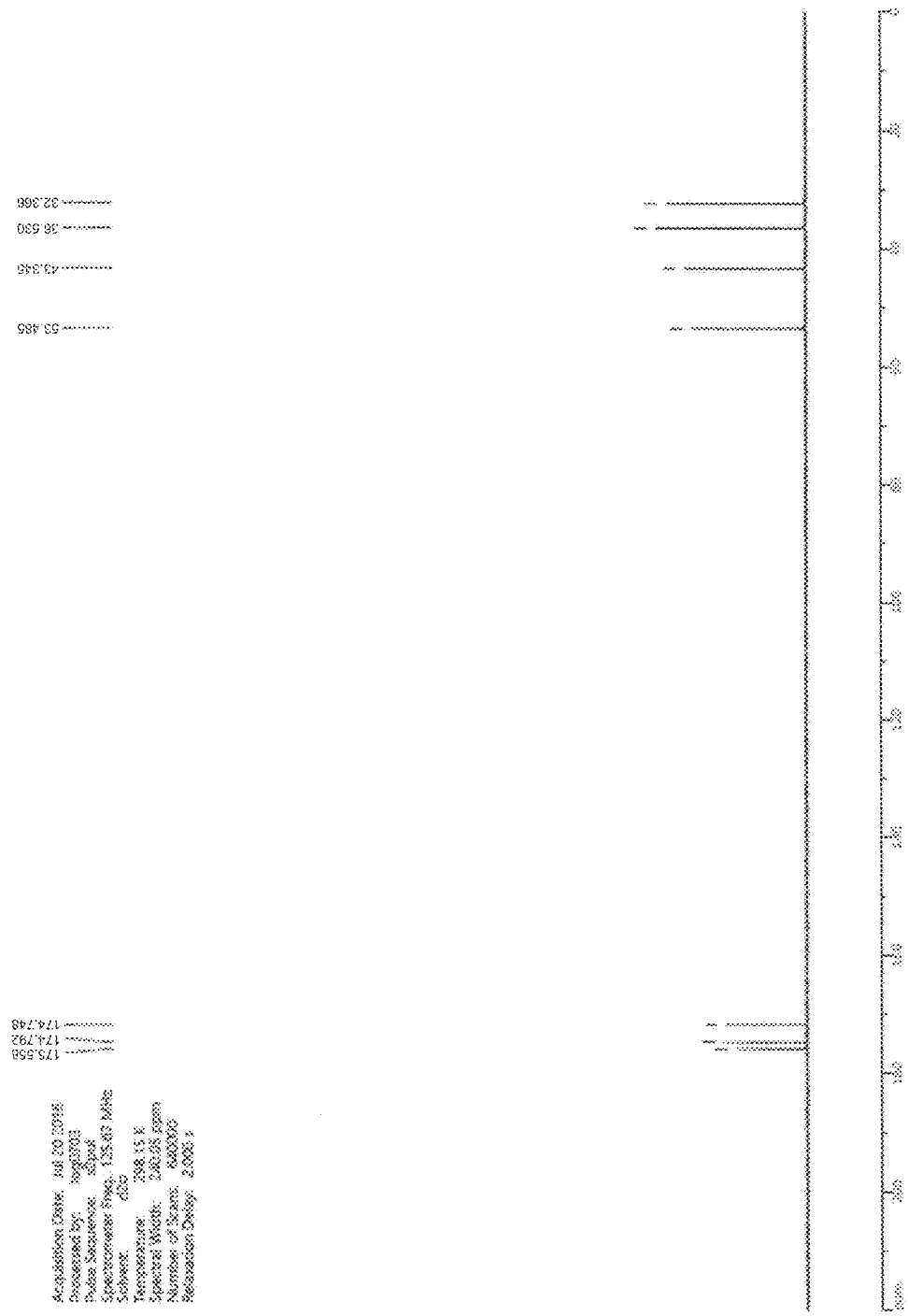
FIG. 3B shows the $^{13}$C NMR spectrum of the stereoisomeric form SAC-A of succinic acid-cysteine (SAC) prepared in Example 3 of the present invention.
Figure 3C:
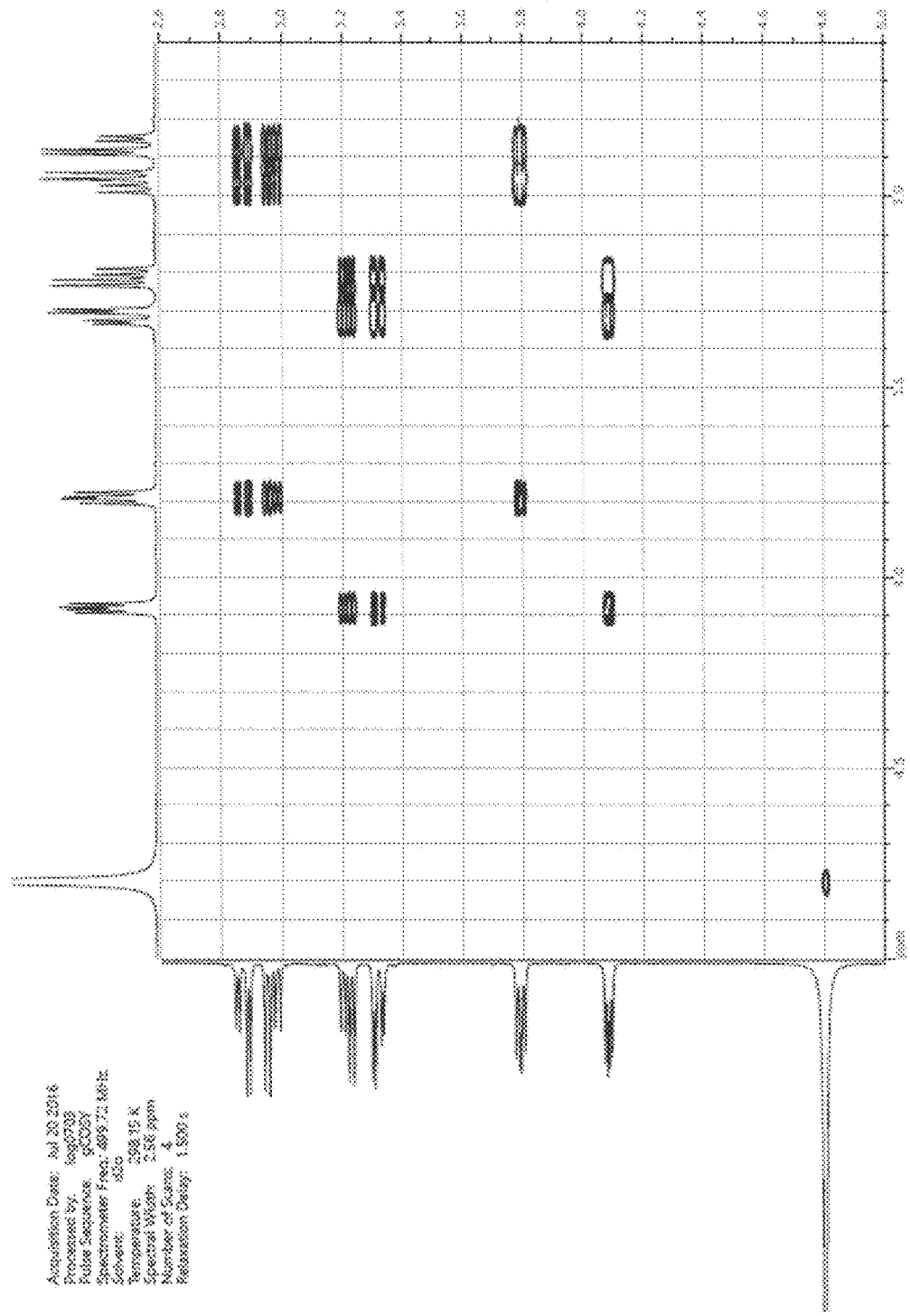
FIG. 3C shows the COSY spectrum of the stereoisomeric form SAC-A of succinic acid-cysteine (SAC) prepared in Example 3 of the present invention.

The compound SAC-A is the stereoisomer of interest, and its $^1$H NMR, $^{13}$C NMR, and COSY spectrums are presented in FIGS. 3A-3C.

FIG. 3A shows the $^1$H NMR spectrum of the stereoisomeric form SAC-A of succinic acid-cysteine (SAC) prepared in Example 3 of the present invention. From FIG. 3A, similar to the proton NMR results for the SAC compound in FIG. 1A, the proton shifts between 2.8 ppm to 3.3 ppm represents the protons attached to the carbon at the $3^{rd}$ position and $5^{th}$ position, while the proton shifts between 3.7 ppm to 4.1 ppm represents the protons attached to the carbon at the $2^{nd}$ position and the $4^{th}$ position (refer to FIG. 1A for the carbon positions). The NMR spectrum is more intense and with less impurities observed.

FIG. 3B shows the $^{13}$C NMR spectrum of the stereoisomeric form SAC-A of succinic acid-cysteine (SAC) prepared in Example 3 of the present invention. From FIG. 3B, similar to the carbon NMR results for the SAC compound in FIG. 1B, the carbon at the $2^{nd}$, $3^{rd}$, $4^{th}$ and $5^{th}$ position have carbon shifts in between 32 ppm to 54 ppm, whereas the three carbonyl carbons at the $1^{st}$, $6^{th}$ and $7^{th}$ position have carbon shifts above 170 ppm (refer to FIG. 1A for the carbon positions). The NMR spectrum is more intense and with less impurities observed.

FIG. 3C shows the COSY spectrum of the stereoisomeric form SAC-A of succinic acid-cysteine (SAC) prepared in Example 3 of the present invention. From FIG. 3C, it can be seen that the two protons having proton shifts between 2.8 ppm to 3.0 ppm have coupling with the one proton located between 3.7 ppm to 3.8 ppm. Furthermore, the two proton shifts between 3.1 ppm to 3.3 ppm have coupling with the one proton located between 4.0 ppm to 4.1 ppm. These results indicate the coupling between a $CH_2$ and an adjacent CH group, which may represent the $CH_2$ group at the $3^{rd}$ position and the $5^{th}$ position having coupling to the adjacent CH group at the $2^{nd}$ position and the $4^{th}$ position. By using the COSY spectrum, the structure of the SAC-A compound can be further confirmed.

FIG. 4 shows the comparison of the $^{13}$C NMR spectrum of two stereoisomeric forms SAC-A and SAC-B of succinic acid-cysteine (SAC) prepared in Example 3 of the present invention. As shown in FIG. 4, there is a slight shift in the position of the $CH_2$ carbons at the $3^{rd}$ position and the $5^{th}$ position and the CH carbons at the $2^{nd}$ position and the $4^{th}$ position between the SAC-A compound and the SAC-B compound. The shift in the peak position can be clearly observed when overlapping the SAC-AB mixture with the SAC-B stereoisomer. From the results above, it proves that the stereoisomers SAC-A and SAC-B are successfully separated, wherein the shift in the peaks may be due to the difference in the stereoisomeric forms.

Figure 5:
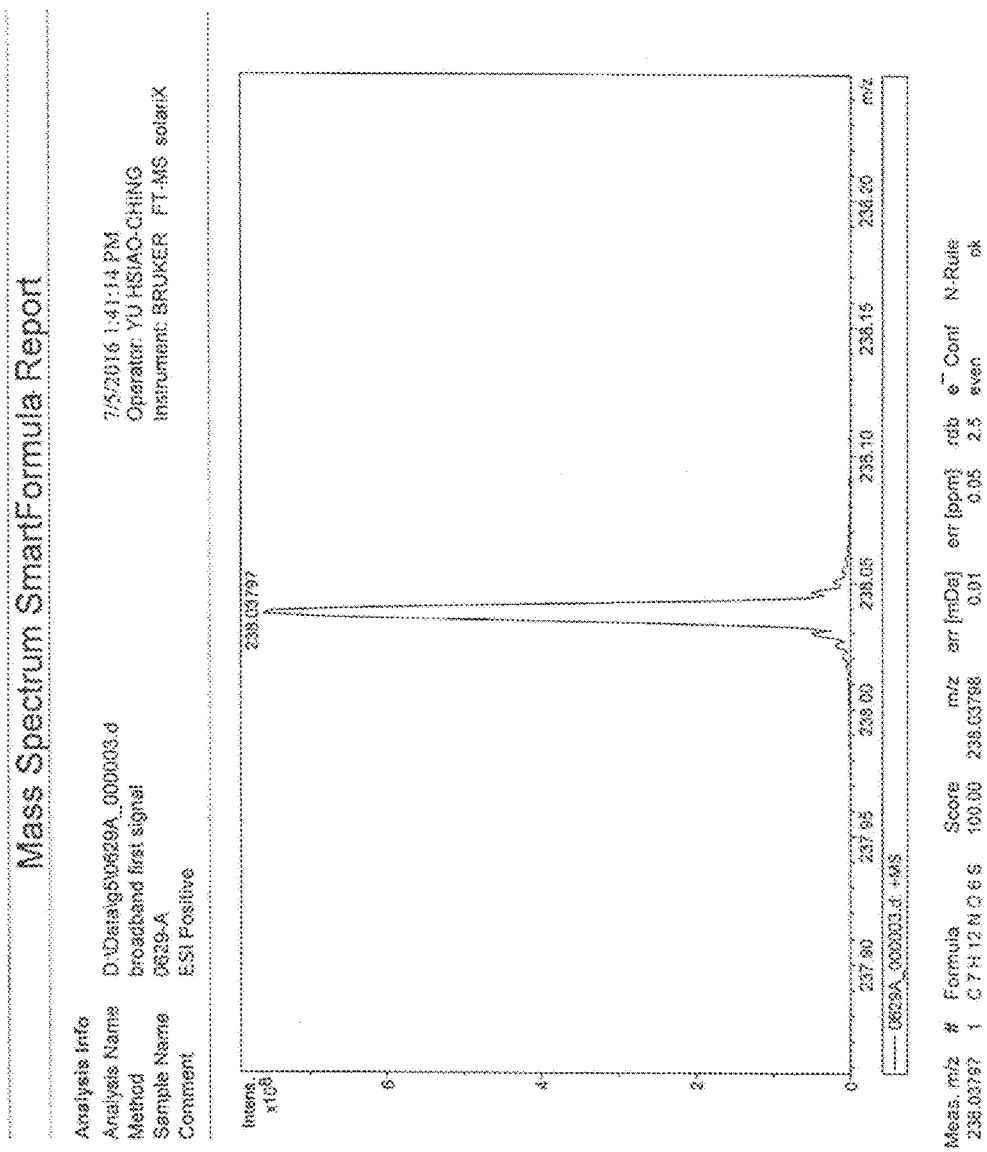
FIG. 5 shows the mass spectrum of the stereoisomeric form SAC-A of succinic acid-cysteine (SAC) prepared in Example 3 of the present invention.

FIG. 5 shows the mass spectrum of the stereoisomeric form SAC-A of succinic acid-cysteine (SAC) prepared in Example 3 of the present invention. As shown in FIG. 5, a sharp peak at 238.03 is observed, which may correspond to the molecular weight of the separated SAC-A compound. Therefore, by using the mass spectrum, it is confirmed that the SAC-A compound is obtained.

Radiolabeling of SAC-A and SAC-B with $^{99m}$TC

For $^{99m}$Tc-labeling, the SAC-A compound (5 mg) and the SAC-B compound (5 mg) were separately dissolved in 0.2 mL of water, and Tin (II) chloride (0.1 mg dissolved in 0.1 mL water) was added thereto at room temperature. Next, sodium pertechnetate Na$^{99m}$TcO$_4$ (5 mCi) was directly added to the above solution. Thereafter, the $^{99m}$Tc-SAC-A and the $^{99m}$Tc-SAC-B compounds are obtained.

The radiochemical purity of the $^{99m}$Tc-SAC-A and the $^{99m}$Tc-SAC-B compounds were determined by radio-thin layer chromatography (ITLC, SG, Gelman Sciences, Ann Arbor, Mich.). The results of the radiochemical purity are presented in FIG. 6A and FIG. 6B.

Figure 6A:
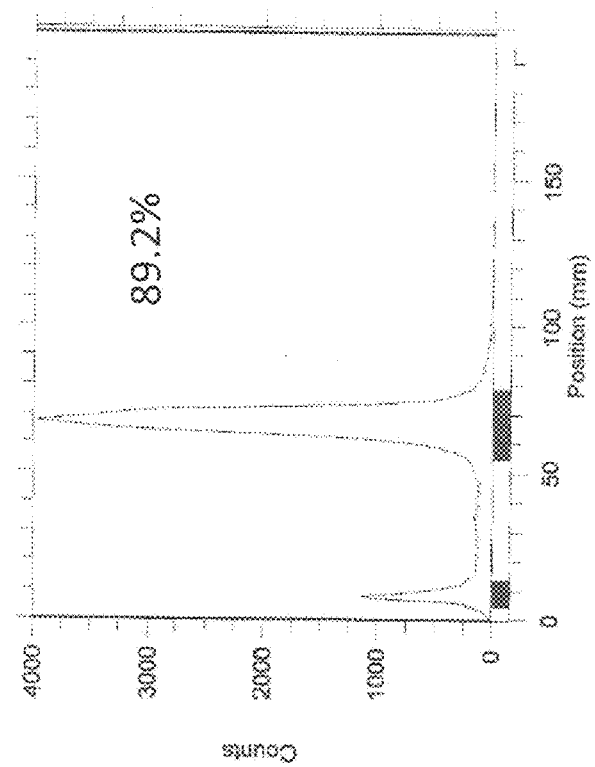
FIG. 6A shows the radiolabeling purity of the stereoisomeric form SAC-A of succinic acid-cysteine (SAC) prepared in Example 3 of the present invention.
Figure 6B:
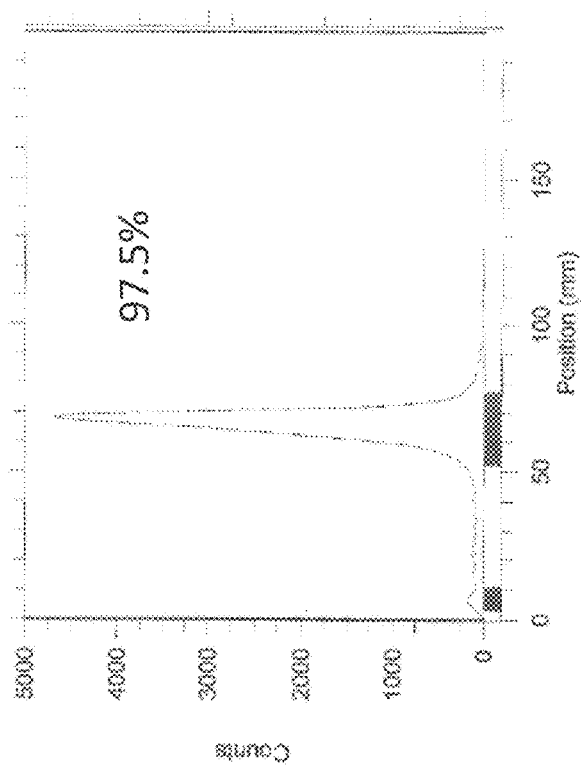
FIG. 6B shows the radiolabeling purity of the stereoisomeric form SAC-B of succinic acid-cysteine (SAC) prepared in Example 3 of the present invention.

FIG. 6A shows the radiolabeling purity of the stereoisomeric form SAC-A of succinic acid-cysteine (SAC) prepared in Example 3 of the present invention. FIG. 6B shows the radiolabeling purity of the stereoisomeric form SAC-B of succinic acid-cysteine (SAC) prepared in Example 3 of the present invention. As shown in FIG. 6A only one clear sharp peak can be observed for the $^{99m}$Tc-SAC-A compound, indicating a radiochemical purity of more than 97.5%. In comparison, two peaks can be observed for the $^{99m}$Tc-SAC-B compound, and the radiochemical purity was only around 89.2%. These results indicated that the SAC-A stereoisomer have a much higher radiolabeling stability as compared to the SAC-B stereoisomer, hence providing a higher radio-chemical yield. Based on the above, it is clear that the SAC-A stereoisomer (compound with formula (IV-a)) is more promising for use in tumor imaging and tumor therapy. Therefore, it is preferable that only one of the stereoisomeric form (SAC-A) is used for conjugation to the metal or the metal-containing compound for radiolabeling and tumor imaging purposes.

It should be noted that the SAC compound containing the two stereoisomeric forms can possibly be used for providing high radiochemical purity. However, from the experiments above, it can be known that the high radio-chemical yield of the SAC compound is mostly attributed to the presence of the SAC-A stereoisomer (compound with formula (IV-a)). Since the amount ratio of the SAC-A stereoisomer to the SAC-B stereoisomer in the SAC compound may be varied and shifted in different samples, a high radiochemical purity cannot be always confirmed. As such, by specifically separating out the SAC-A stereoisomeric form, a high radio-chemical purity and radiolabeling efficiency can be guaranteed.

Based on the above, the compound represented by formula (I) of the invention was shown to have improved specificity to tumor cells (cellular uptake to nucleus), and is therefore suitable for carrying anti-cancer drugs and/or nuclear imaging agents. Moreover, it is preferable that the compound of formula (I) is obtained by conjugating the metal or the metal-containing compound M to a compound represented by formula (IV), wherein only one one of the stereoisomeric forms of formula (IV) is used for conjugation to the metal or the metal-containing compound M. As such, when one of the stereoisomeric form (SAC-A) is used for conjugation, the resulting compound can have a higher radiolabeling stability, and is therefore more desirable for use in tumor imaging and tumor therapy.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A compound represented by formula (I):

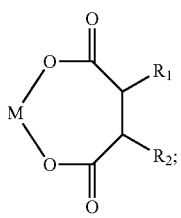

formula (I)

in formula (I), $R_1$ and $R_2$ each independently represents hydrogen, O—$R_3$ or S—$R_4$, wherein at least one of $R_1$ and $R_2$ is O—$R_3$ or S—$R_4$, and $R_3$ and $R_4$ are independently a $C_1$ to $C_{10}$ alkyl group, such that the $C_1$ to $C_{10}$ alkyl group is non-substituted or substituted with at least one selected from the group consisting of —OH, —$NH_2$, halogen, ester, ether, and carboxylic acid; and wherein M is a metal or a metal-containing compound.

2. The compound according to claim 1, wherein the metal or the metal-containing compound M is $^{99m}Tc$, $^{117m}Sn$, $^{188}Re$, $^{186}Re$, $^{90}Y$, $^{67}Ga$, $^{68}Ga$, $^{66}Ho$, $^{153}Sm$, $^{59}Fe$, $^{60}Cu$, $^{61}Cu$, $^{67}Cu$, $^{64}Cu$, $^{62}Cu$, $^{187}Re$, $^{89}Y$, $^{69}Ga$, $^{153}Pt$, $^{27}Al$, $^{56}Fe$, $^{64}Cu$, $^{118}Sn$, $^{10}B$, $^{58}Co$, $^{79}Se$, $^{40}Ca$, $^{64}Zn$, $^{157}Gd$, or a combination thereof.

3. The compound according to claim 1, wherein one of $R_1$ and $R_2$ is hydrogen and the other one is S—$R_3$.

4. The compound according to claim 3, wherein S—$R_3$ is cysteine.

5. The compound according to claim 1, wherein the compound is further represented by formula (II) or formula (III):

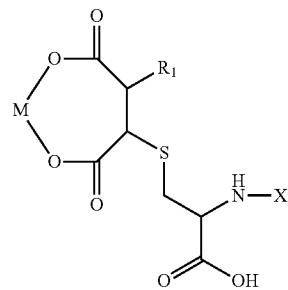

formula (II)

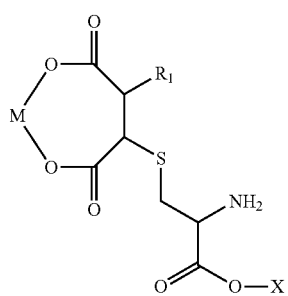

formula (III)

wherein in formula (II) and formula (III), X is an anti-cancer drug, an antiviral drug, an antibacterial drug, or a combination thereof.

6. The compound according to claim 5, wherein the drug X is melphalan, chlorambucil, methotrexate, paclitaxel, metronidazole, doxorubicin, penciclovir, ganciclovir, acyclovir, anti-EGFR antibody, anti-VEGF antibody, anti-PDGF antibody, retinoic acid, RGD peptide, or octreotide.

7. The compound according to claim 1, wherein the compound of formula (I) is obtained by conjugating the metal or the metal-containing compound M to a compound represented by formula (IV),

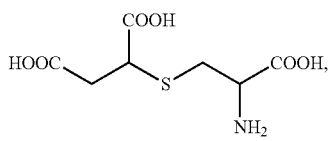

formula (IV)

wherein the compound represented by formula (IV) has two stereoisomeric forms and only one of the stereoisomeric form is used for conjugation to the metal or the metal-containing compound M.

8. The compound according to claim 7, wherein the two stereoisomeric forms of formula (IV) is represented by formula (IV-a) and formula (IV-b):

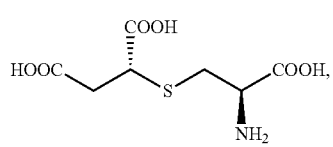

formula (IV-a)

-continued

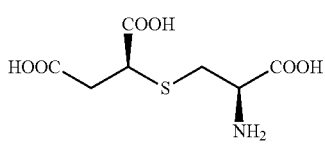
formula (IV-b)

wherein only the stereoisomeric form represented by formula (IV-a) is used for conjugation to the metal or the metal-containing compound M.

9. A pharmaceutical composition for tumor imaging and/or tumor therapy, comprising:
a pharmaceutically-acceptable carrier; and
a compound represented by formula (I):

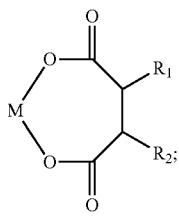
formula (I)

in formula (I), $R_1$ and $R_2$ each independently represents hydrogen, O—$R_3$ or S—$R_4$, wherein at least one of $R_1$ and $R_2$ is O—$R_3$ or S—$R_4$, and $R_3$ and $R_4$ are independently a $C_1$ to $C_{10}$ alkyl group, such that the $C_1$ to $C_{10}$ alkyl group is non-substituted or substituted with at least one selected from the group consisting of —OH, —$NH_2$, halogen, ester, ether, and carboxylic acid; and M is a metal or a metal-containing compound.

10. The pharmaceutical composition according to claim 9, wherein the metal or the metal-containing compound M is $^{99m}$Tc, $^{117m}$Sn, $^{188}$Re, $^{186}$Re, $^{90}$Y, $^{67}$Ga, $^{68}$Ga, $^{166}$Ho, $^{153}$Sm, $^{59}$Fe, $^{60}$Cu, $^{61}$Cu, $^{67}$Cu, $^{64}$Cu, $^{62}$Cu, $^{187}$Re, $^{89}$Y, $^{69}$Ga, $^{153}$Pt, $^{27}$Al, $^{56}$Fe, $^{64}$Cu, $^{118}$Sn, $^{10}$B, $^{58}$Co, $^{79}$Se, $^{40}$Ca, $^{64}$Zn, $^{157}$Gd, or a combination thereof.

11. The pharmaceutical composition according to claim 9, wherein one of $R_1$ and $R_2$ is hydrogen and the other one is S—$R_3$.

12. The pharmaceutical composition according to claim 11, wherein S—$R_3$ is cysteine.

13. The pharmaceutical composition according to claim 9, wherein the compound is further represented by formula (II) or formula (III):

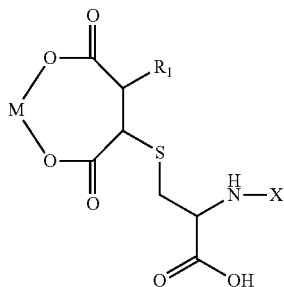
formula (II)

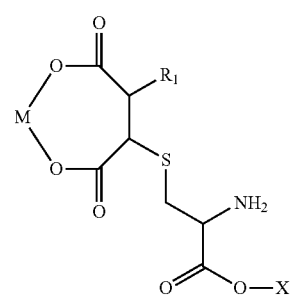
formula (III)

wherein in formula (II) and formula (III), X is an anti-cancer drug, an antiviral drug, an antibacterial drug, or a combination thereof.

14. The pharmaceutical composition according to claim 13, wherein the drug X is melphalan, chlorambucil, methotrexate, paclitaxel, metronidazole, doxorubicin, penciclovir, ganciclovir, acyclovir, anti-EGFR antibody, anti-VEGF antibody, anti-PDGF antibody, retinoic acid, RGD peptide, or octreotide.

15. The pharmaceutical composition according to claim 9, wherein the compound of formula (I) is obtained by conjugating the metal or the metal-containing compound M to a compound represented by formula (IV),

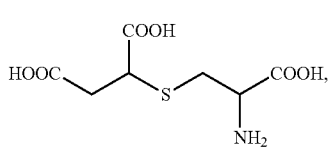
formula (IV)

wherein the compound represented by formula (IV) has two stereoisomeric forms and only one of the stereoisomeric form is used for conjugation to the metal or the metal-containing compound M.

16. The pharmaceutical composition according to claim 15, wherein the two stereoisomeric forms of formula (IV) is represented by formula (IV-a) and formula (IV-b):

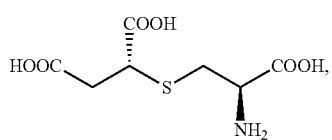
formula (IV-a)

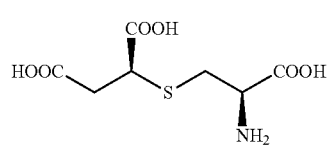
formula (IV-b)

wherein only the stereoisomeric form represented by formula (IV-a) is used for conjugation to the metal or the metal-containing compound M.

* * * * *